United States Patent [19]
Cugnon de Sevricourt et al.

[11] Patent Number: 5,571,843
[45] Date of Patent: Nov. 5, 1996

[54] DERIVATIVES OF INDAN-1,3-DIONE AND INDAN-1,2,3-TRIONE, METHODS OF PREPARING THEM AND THERAPEUTIC USE THEREOF

[75] Inventors: Michel P. Cugnon de Sevricourt, Moult; Catherine G. Dacquet, Paris; Michel A. Finet, Fresnes; Florence J. Le Marquer; Max F. Robba, both of Paris; Norbert O. Tembo, Cergy St Christophe; Sylvie J. Yannic-Arnoult, Grigny; Jean-Luc Torregrosa, Saint-Denis, all of France

[73] Assignee: Innothera, Arcueil, France

[21] Appl. No.: 142,479

[22] PCT Filed: Apr. 1, 1993

[86] PCT No.: PCT/FR93/00328

§ 371 Date: Mar. 24, 1994

§ 102(e) Date: Mar. 24, 1994

[87] PCT Pub. No.: WO93/20045

PCT Pub. Date: Oct. 14, 1993

[30] Foreign Application Priority Data

Apr. 3, 1992 [FR] France ................ 92 04071

[51] Int. Cl.⁶ .............. A61K 31/175; C07C 281/06
[52] U.S. Cl. .............. 514/590; 514/352; 514/353; 514/581; 514/582; 546/304; 546/306; 564/18; 564/19; 564/20; 564/34; 564/36
[58] Field of Search .............. 564/18, 19, 20, 564/34, 36; 514/581, 582, 590, 352, 353; 546/304, 306

[56] References Cited

U.S. PATENT DOCUMENTS

3,280,185 10/1966 Wendt et al. .............. 260/552

FOREIGN PATENT DOCUMENTS

0172128 2/1986 European Pat. Off. .
0236151 9/1987 European Pat. Off. .
0456133 11/1991 European Pat. Off. .
2127982 12/1972 Germany .
9320045 10/1993 WIPO .

OTHER PUBLICATIONS

Matthies et. al, Synthesis, 1972, 154–155.
CA 107890, 1967 (Abstract only).
Varma et. al, J. Pharmaceutical Sciences, 1967, 775–776.
CA 120286 s, 1974 (Abstract only).
CA 43946 q, 1976 (Abstract only).
CA 9584 q, 1975 (Abstract only).
CA 55040 (e & f), 1970 (Abstract only).
Ishai et. al, J. Org. Chem. vol. 38, No. 12, 1973, 2251–52.

*Primary Examiner*—Shailendra Kumar
*Attorney, Agent, or Firm*—Finnegan, Henderson, Farabow, Garrett & Dunner

[57] ABSTRACT

Therapeutic compounds having the formula:

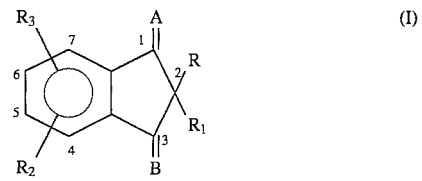

in which $R_2$ and $R_3$ independently denote H, $C_1$–$C_4$ alkoxy or OH and (A, B)=(oxygen, oxygen) in which case one out of R and $R_1$ denotes OH, halogen, secondary amino or tertiary amine and the other denotes $NHNHCONHR_4$ or R and $R_1$ together denote =N—NH—CX—$NHR_5$, =N—NH—CX—N(phenyl)$_2$, =N—NH—CX—NH—NH—$R_5$, =N—NH—C(SCH$_3$)=N—$R_6$ or =N—N=C(SCH$_3$)—NH—$R_6$; or (A, B)=(N—OH, oxygen) in which case R and $R_1$ together form =N—NH—CX—$NHR_5$ or =N—NH—CX—N(phenyl)$_2$; or (A, B)=(N—NH—CX—$NHR_5$, oxygen) in which case R and $R_1$ together form =N—NH—CX—$NHR_5$; or (A,B)=(N—OH, N—OH) in which case R and $R_1$ together form =N—NH—CX—$NHR_5$ or =N—NH—CX—N(phenyl)$_2$.

15 Claims, No Drawings

DERIVATIVES OF INDAN-1,3-DIONE AND INDAN-1,2,3-TRIONE, METHODS OF PREPARING THEM AND THERAPEUTIC USE THEREOF

This application is a 371 of PCT/FR93/00328, filed Apr. 1, 1993.

The invention relates to novel derivatives of indan-1,2-dione and indan-1,2,3-trione, methods of preparation thereof and use thereof in therapy.

More specifically, these derivatives have the formula:

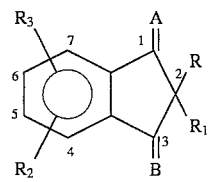  (I)

in which $R_2$ and $R_3$ independently denote H, $C_1$–$C_4$ alkoxy or OH, and the pair (A, B) denotes either:

(oxygen, oxygen), in which case one out of R and $R_1$ denotes OH, halogen, ($C_1$–$C_4$ alkyl) NH, N-morpholino($C_1$–$C_4$ alkyl) NH, 1-(pyridyl)-4-piperazino or 1-(phenyl)-4-piperazino in which the phenyl ring is optionally substituted by a halogen, and the other denotes an NHNHCONHR$_4$ group where $R_4$=phenyl or phenyl substituted by OH or $C_1$–$C_4$ alkyl and R and $R_1$ may also together form a group, i.e.:

=N—NH—CX—NHR$_5$ where X represents oxygen or sulphur and $R_5$=H, pyridyl, phenyl or phenyl substituted by one, two or three groups chosen from among OH, CF$_3$, $C_1$–$C_4$ alkyl, $C_1$–$C_4$ alkoxy, halogen, methylene dioxy, acetoxy or hydroxyethyl, or =NNHCXN (phenyl)$_2$, where X denotes oxygen or sulphur or =N—NH—CX—NH—NH—R$_5$ where X and $R_5$ have the same meanings as hereinbefore, or =N—NH—C(SCH$_3$)=NR$_6$ or =N—N=C(SCH$_3$)—NHR$_6$ where $R_6$ denotes phenyl or phenyl substituted by one, two or three groups chosen from among OH, CF$_3$, $C_1$–$C_4$ alkyl, $C_1$–$C_4$ alkoxy, halogen, methylene dioxy, acetoxy or hydroxyethyl or (N—OH, oxygen) in which case R and $R_1$ together form an =NNHCXNHR$_5$ or =NNHCXN (phenyl)$_2$ group, where X and $R_5$ have the same meanings as hereinbefore, or (NNHCXNHR$_5$, oxygen), where X and $R_5$ have the same meanings as hereinbefore, in which case R and $R_1$ together form an =NNHCXNHR$_5$ group or (N—OH, N—OH), in which case R and $R_1$ together form an =NNHCXNHR$_5$ group where X and $R_5$ have the same meanings as hereinbefore, or an =N—NH—CX—N (phenyl)$_2$.

Formula (I) hereinbefore includes:

(i) compounds having the formula:

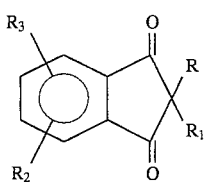  (I')

where R, $R_1$, $R_2$ and $R_3$ have the same meanings as in formula (I) when the pair (A, B) therein denotes (oxygen, oxygen), (ii) compounds having the formula:

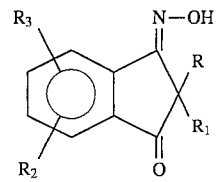  (I'')

where R, $R_1$, $R_2$ and $R_3$ have the same meanings as in formula (I), when the pair (A, B) therein denotes (=N—OH, oxygen), (iii) compounds having the formula:

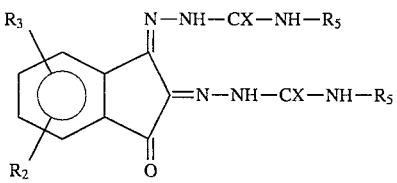  (I''')

where $R_2$, $R_3$, X and $R_5$ have the same meanings as in formula (I), and (iv) compounds having the formula:

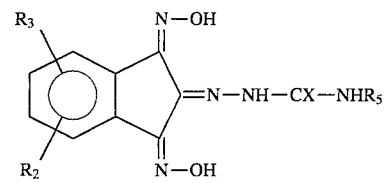  (I'''')

where $R_2$, $R_3$, X and $R_5$ have the same meanings as in formula (I).

Formula (I) hereinbefore includes:

(a) compounds having the formula:

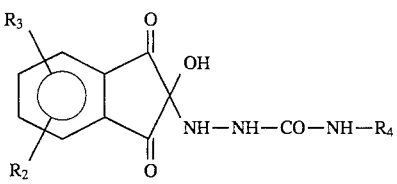  (Ia)

(b) compounds having the formula:

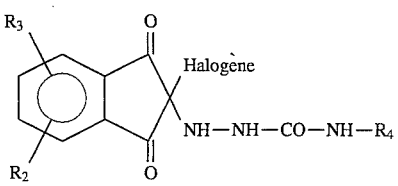  (Ib)

(c) compounds having the formula:

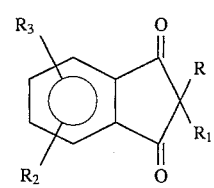  (Ic)

where one out of R and $R_1$ denotes NHNHCONHR$_4$ and the other denotes ($C_1$–$C_4$ alkyl) NH, N-morpholino ($C_1$–$C_4$ alkyl) NH, 1-(pyridyl)-4-piperazino or 1-(phenyl)-4-piperazino in which the phenyl ring is optionally substituted by a halogen, (d) compounds having the formula:

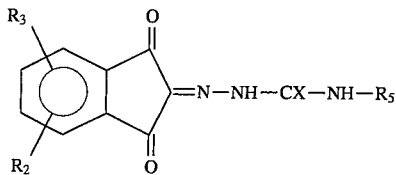
(Id)

(e) compounds having the formula:

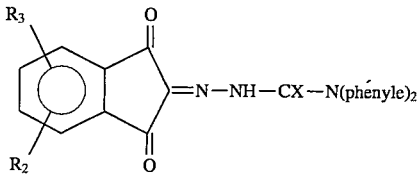
(Ie)

(f) compounds having the formula:

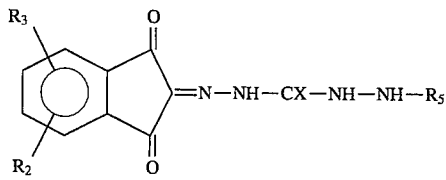
(If)

(g) compounds having the formula:

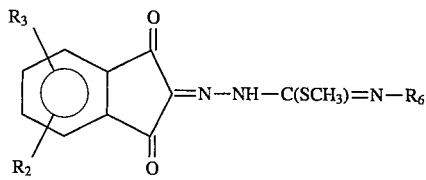
(Ig)

(h) compounds having the formula:

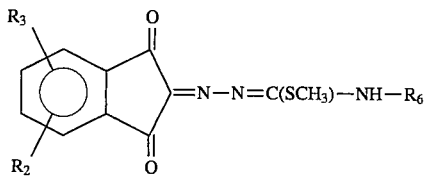
(Ih)

(i) compounds having the formula:

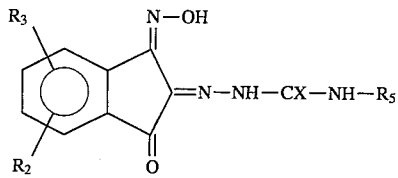
(Ii)

(j) compounds having the formula:

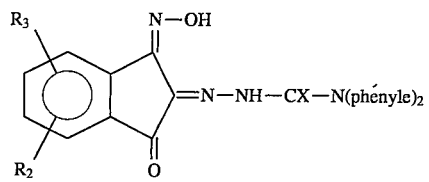
(Ij)

(k) compounds having the formula:

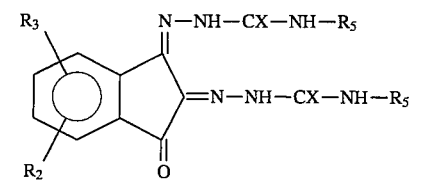
(Ik)

(l) compounds having the formula:

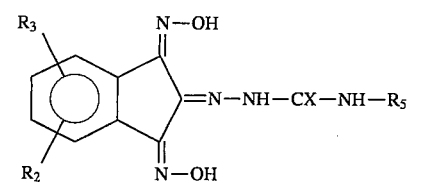
(Il)

and (m) compounds having the formula:

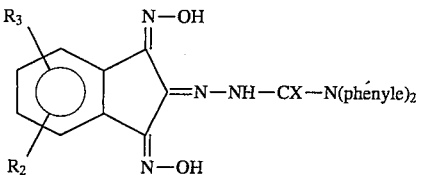
(Im)

in which the symbols $R_2$, $R_3$, $R_4$, $R_5$ and X have the same meanings as in formula (I).

In formulae (I') to (I'''') and (Ia) to (Im) hereinbefore, $R_2$ is inter alia in position 5 and $R_3$ in position 6.

Also, in formulae (I') to (I'''') and (Ia) to (Im), the pair ($R_2$, $R_3$) may inter alia be (H, H), (5—$OCH_3$,H), (5—OH, H) or (5—$OCH_3$, 6—$OCH_3$).

The invention also covers salts of the salt-forming compounds among those described hereinbefore. These salts comprise addition salts of mineral acids such as hydrochloric, hydrobromic, sulphuric or phosphoric acid, and addition salts of organic acids such as acetic, propionic, oxalic or citric acid.

The invention also covers all possible stereoisomers of formula (I) derivatives and mixtures of such stereoisomers, as well as the metabolites of these derivatives.

The invention also covers methods of preparing formula (I) derivatives. These methods are described in diagrams 1 to 6 hereinafter, in which the symbols R to $R_6$ and X, unless stated otherwise, have the same meanings as in formula (I).

Diagram 1
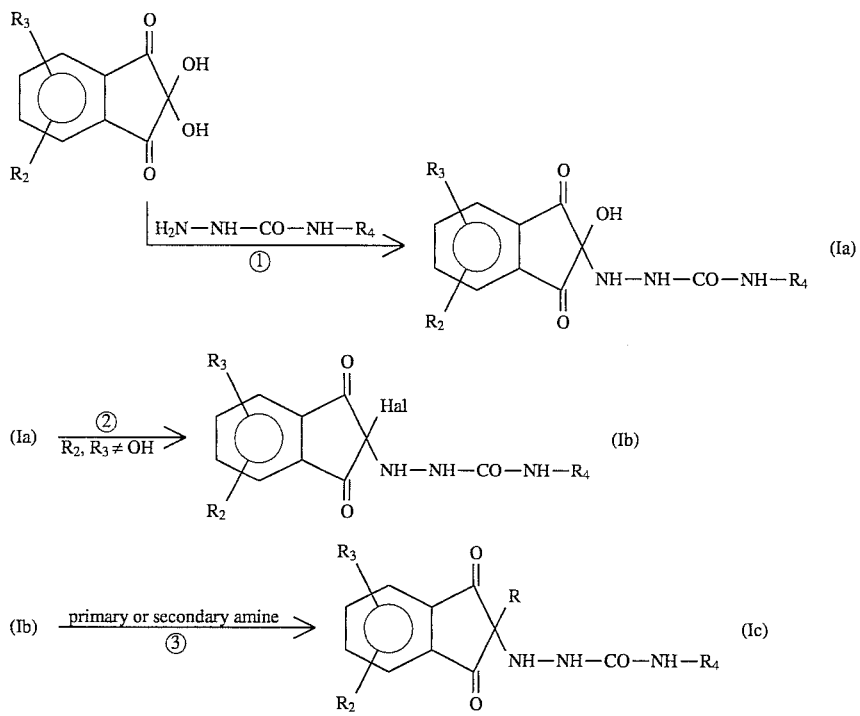
R ≠ OH, halogen
Hal: halogen
Diagram 2
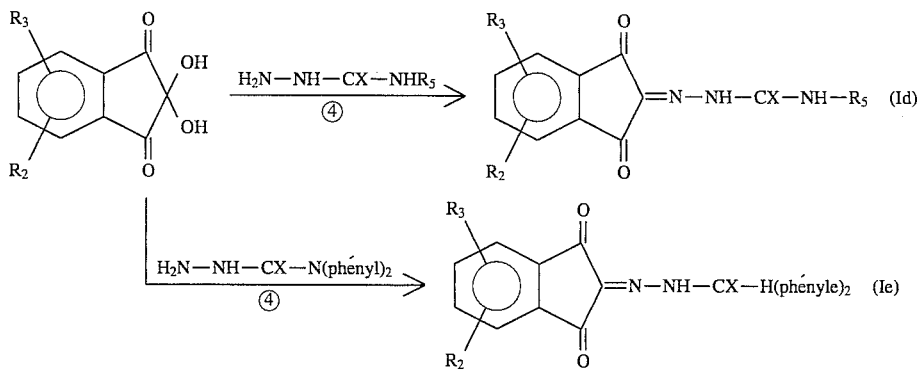
Diagram 3
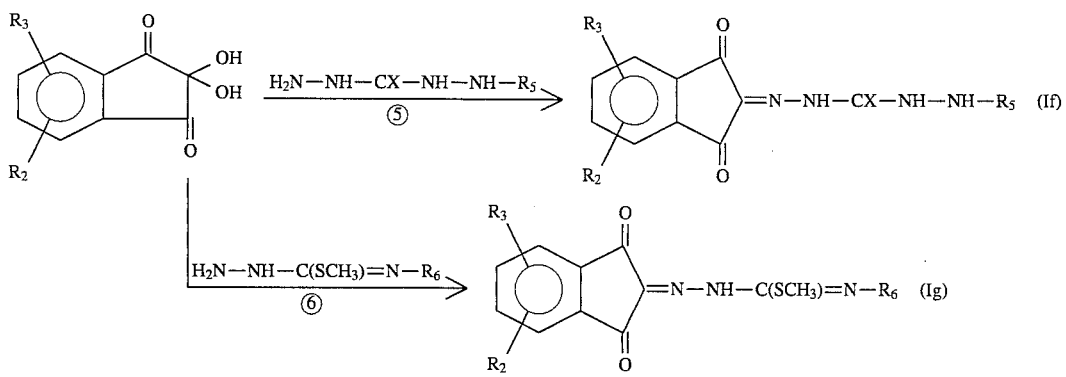

Diagram 4

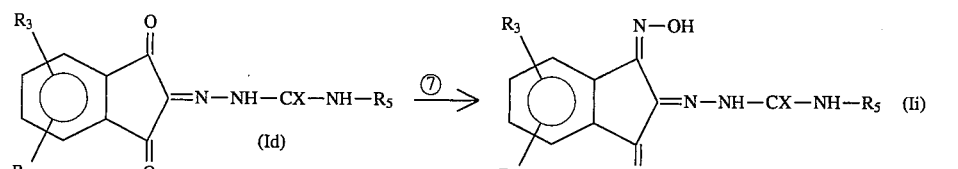

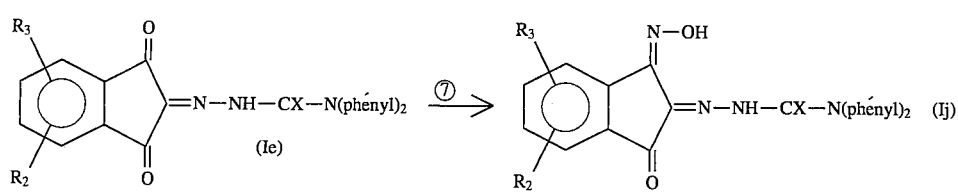

Diagram 5

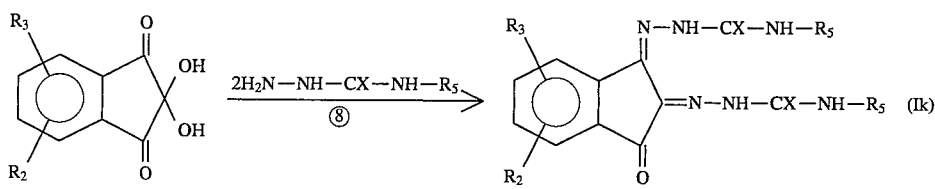

Diagram 6

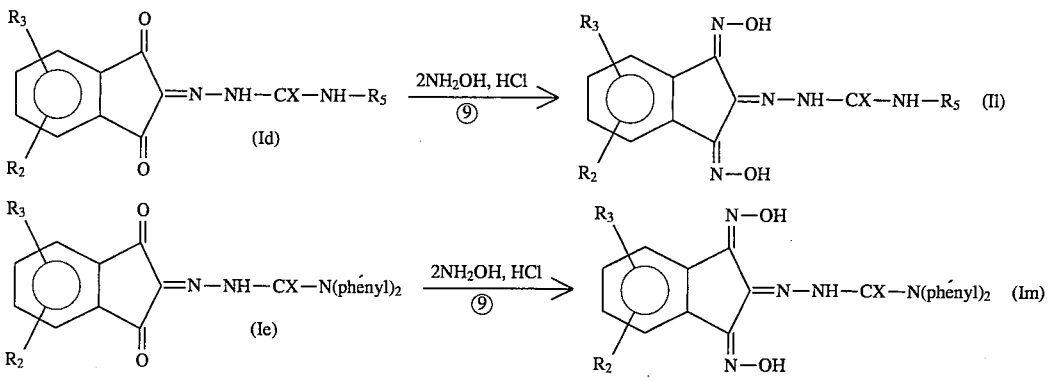

In the diagrams hereinbefore, ① to ⑨ denote the methods used and have the following meanings:

① Condensation in a solvent such as ethanol, hot and preferably refluxed.

② Reaction with a halogenating agent, inter alia a chlorinating agent, preferably thionyl chloride, in a solvent such as THF, hot and preferably refluxed.

③ Condensation with a primary amine [($C_1$–$C_4$ alkyl)$NH_2$ or N-morpholino($C_1$–$C_4$ alkyl) $NH_2$] or a secondary amine [1-pyridyl-4-piperazine or 1-(phenyl)-4-piperazine in which the phenyl ring is optionally substituted by a halogen atom] in a solvent such as diethyl ether, in the presence of a base such as triethylamine.

④ Condensation of the semicarbazide or thiosemicarbazide in hydrochloride form in a solvent such as an ethanol-water mixture, hot and preferably refluxed, or Condensation of the semicarbazide or thiosemicarbazide in a solvent such as ethanol, preferably at ambient temperature.

⑤ Condensation in a solvent, inter alia an aqueous solution of ethanol, preferably at ambient temperature, followed by treatment of the reaction product with HCl in ethanol.

⑥ Condensation in a solvent, inter alia an aqueous solution of ethanol, hot. Note that the (Ig) formula compounds may also exist in the tautomeric form (Ih).

⑦ Condensation with hydroxylamine hydrochloride in the presence of sodium acetate and in a solvent such as aqueous ethanol, hot and preferably refluxed.

⑧ The same reaction conditions as in ④ but using two equivalents of semicarbazide or thiosemicarbazide.

⑨ Hot condensation preferably with reflux in a solvent such as aqueous ethanol, in the presence of sodium acetate.

The following preparations are given by way of example to illustrate the invention.

A. Preparation of the Raw Materials

EXAMPLE A 5-hydroxyindan-1,3-dione 4 ml of 10N sulphuric acid were added to a suspension of 0.01 mol of 5-acetoxy-2-carbethoxy-3-hydroxy-1-indanone in 80 ml water. The reaction mixture was refluxed for 15 minutes. The insoluble substance was filtered when hot and the yellow precipitate formed after cooling was dried on vacuo pump, washed in ice water and dried.

Yield: 85%; M.P.: 208° C.; IR: $\upsilon$ OH=3250 cm$^{-1}$, $\upsilon$ CO=1730 and 1680 cm$^{-1}$.

EXAMPLE B 2-bromo-5-hydroxyindan-1,3-dione 0.02 mol bromine was added dropwise to a solution of 0.02 mol of 5-hydroxyindan-1,3-dione in 60 ml chloroform. The reaction mixture was agitated at 50° C. for 30 minutes and the precipitate obtained after evaporation of the solvent was recrystallised.

Yield: 60%; M.P.: 194° C.; IR: $\upsilon$ OH=3380 cm$^{-1}$, $\upsilon$ CO=1740 and 1710 cm$^{-1}$.

Recrystallisation solvent: a mixture (V/V) of ethyl ether and petroleum ether.

EXAMPLE C 5-hydroxyindan-1,2,3-trione, monohydrate

A solution of 0.01 mol of 2-bromo-5-hydroxyindan-1,3-dione in 10 ml dimethyl sulphoxide was heated to 80° C. for 30 minutes. 50 ml of a 1N hydrochloric acid solution was added, after which heating was continued for 30 minutes. The oily suspension obtained after cooling was extracted with ethyl ether. The organic phase was washed in water and dried over magnesium sulphate.

The yellow precipitate obtained after evaporation of the solvent was recrystallised from water.

Yield: 45%; M.P.>265° C.; IR: $\upsilon$ OH=3340 cm$^{-1}$, $\upsilon$ CO=1750 and 1710 cm$^{-1}$.

EXAMPLE D 5,6-dimethoxyindan-1,2,3-trione, monohydrate 0.06 mol of selenium oxide in solution in 2.5 ml water was added to a solution of 0.03 mol of 5,6-dimethoxy-1-indanone in 100 ml dioxan. The reaction mixture was refluxed for 7 hours and the residue obtained after evaporation of the solvent was dissolved in ethyl acetate. The organic phase was washed several times in water, dried over magnesium sulphate and decolorized.

The precipitate obtained after evaporation of the solvent was recrystallised from ethyl ether.

Yield: 50%; M.P.: 170° C.; IR: $\upsilon$ CO=1730 and 1700 cm$^{-1}$.

EXAMPLE E 6-hydroxy-5-methoxyindan-1,2,3-trione, monohydrate 0.06 mol of selenium oxide in solution in 2.5 ml water was added to a solution of 0.03 mol of 6-hydroxy-5-methoxy-1-indanone in 100 ml dioxan. The reaction mixture was refluxed for 7 hours and the residue obtained after evaporation of the solvent was dissolved in ethyl acetate. The organic phase was washed several times in water, dried over magnesium sulphate and decolorized.

The precipitate obtained after evaporation of the solvent was recrystallised from water.

Yield: 50%; M.P.>265° C.; IR: $\upsilon$ CO=1740 and 1700 cm$^{-1}$.

EXAMPLE F 2-oximino-5-hydroxyindan-1,3-dione 0.02 mol of sodium nitrite in solution in 8 ml water was added dropwise, keeping the temperature at 5° C., to a suspension of 0.01 mol of 5-hydroxyindan-1,3-dione in 6 ml of 2N sulphuric acid solution. The reaction mixture was agitated at 5° C. for 4 hours. The insoluble substance was dried on suction pump, washed in water, dried and recrystallised from acetone.

Yield: 65%; M.P.: 220° C.; IR: $\upsilon$ OH=3400 and 3260 cm$^{-1}$, $\upsilon$ CO=1730 and 1690 cm$^{-1}$.

Reference hereinafter is made to ninhydrin. Note that this substance is also known under the name indan-1,2,3-trione monohydrate or the name of 2,2-dihydroxy-1,3-dioxo-2H-indene. These three names are used without distinction hereinbefore and hereinafter.

B. Preparation of formula (Ia) and (Ib) compounds

METHOD 1

0.01 mol of $H_2N$—NH—CO—NH—$R_5$ in solution in 20 ml ethanol was added to a solution of 0.01 mol of optionally substituted ninhydrin in 20 ml ethanol. The reaction mixture was heated to 60° C. for 5 to 15 minutes and the resulting white precipitate was dried on suction pump, washed in ethyl ether and dried.

METHOD 2

3.5 ml (0.04 mol) of thionyl chloride was added dropwise to a solution of 0.02 mol of the compound obtained by method 1 in 20 ml tetrahydrofuran. The reaction mixture was refluxed for an hour. The residual oil obtained after evaporating the excess thionyl chloride and tetrahydrofuran crystallised after washing in petroleum ether.

EXAMPLE 1

2-hydroxy-2-[4(2-hydroxyphenyl)-semicarbazido]indan-1,3-dione

METHOD 1

Raw materials: ninhydrin and 4-(hydroxyphenyl)-semicarbazide hydrochloride. Yield: 90%; M.P. 190° C.; IR: $\upsilon$ OH=3400 cm$^{-1}$, $\upsilon$ NH=3210 cm$^{-1}$, $\upsilon$ CO=1760, 1720 and 1640 cm$^{-1}$.

C. Preparation of formula (Ic) compounds

METHOD 3

1 ml of triethylamine was added to a solution of 0.007 mol of formula (Ib) compound in 60 ml ethyl ether. The mixture was agitated for 5 minutes, then 0.007 mol of amine was added. The reaction mixture was agitated at ambient temperature for 2 hours. The resulting precipitate was dried on suction pump, repeatedly washed in water, dried and recrystallised.

D. Preparation of formula (Id) and (Ie) compounds

METHOD 4

0.01 mol of the corresponding semicarbazide (or thiosemicarbazide) hydrochloride in solution in 10 ml water was added to a solution of 0.01 mol of optionally substituted ninhydrin in 50 ml ethanol.

The reaction mixture was refluxed for 1 hour (or 30 minutes in examples 11 to 14). The precipitate formed was dried on suction pump when hot (or cold in examples 12 to 15), dried and recrystallised.

In the case where the precipitate was a mixture of mono and disubstituted compounds, separation was brought about by fractional recrystallisation.

EXAMPLE 2

2-semicarbazono-indan-1,3-dione

Raw materials: ninhydrin, semicarbazide hydrochloride.

Yield: 70%; M.P. 255° C.; IR: $\upsilon$ $NH_2$ and NH=3450, 3350 and 3220 $cm^{-1}$, $\upsilon$ CO=1720 and 1680 $cm^{-1}$.

Recrystallisation solvent: acetonitrile.

EXAMPLE 3

2-(4-phenyl semicarbazono)-indan-1,3-dione

Raw materials: ninhydrin, 4-phenyl semicarbazide hydrochloride.

Yield: 40%; M.P. 220° C.; IR: $\upsilon$ NH=3350 and 3250 $cm^{-1}$, $\upsilon$ CO=1730, 1715 and 1680 $cm^{-1}$.

Recrystallisation solvent: ethyl acetate

EXAMPLE 4

2-[4-(2-hydroxyphenyl)-semicarbazono]indan-1,3-dione

Raw materials: ninhydrin, 4-(2-hydroxyphenyl)-semicarbazide hydrochloride

Yield: 50%; M.P. 260° C.; IR: $\upsilon$ OH=3460 $cm^{-1}$, $\upsilon$ NH=3370 and 3250 $cm^{-1}$, $\upsilon$ CO=1735 and 1680 $cm^{-1}$.

Recrystallisation solvent: ethanol

EXAMPLE 5

2-(4-phenyl thiosemicarbazono)-indan-1,3-dione

Raw materials: ninhydrin, 4-phenyl thiosemicarbazide hydrochloride

Yield: 45%; M.P. 222° C.; IR: $\upsilon$ NH=3360 and 3240 $cm^{-1}$, $\upsilon$ CO=1730 and 1680 $cm^{-1}$.

Recrystallisation solvent: ethanol.

EXAMPLE 6

2-[4-(2-methoxyphenyl)-semicarbazono]indan-1,3-dione

Raw materials: ninhydrin, 4-(2-methoxyphenyl)-semicarbazide hydrochloride.

Yield: 80%; M.P. 235° C.; IR: $\upsilon$ NH=3360 and 3240 $cm^{-1}$, $\upsilon$ CO=1730 and 1690 $cm^{-1}$.

Recrystallisation solvent: methanol

EXAMPLE 7

2-[4-(3-methoxyphenyl)-semicarbazono]indan-1,3-dione monohydrate

Raw materials: ninhydrin, 4-(3-methoxyphenyl)-semicarbazide hydrochloride

Yield: 70%; M.P. 195° C.; IR: $\upsilon$ OH=3600 and 3500 $cm^{-1}$, $\upsilon$ NH=3260 $cm^{-1}$, $\upsilon$ CO=1725 and 1680 $cm^{-1}$.

Recrystallisation solvent: ethanol

EXAMPLE 8

2-[4-(4-methoxyphenyl)-semicarbazono]indan-1,3-dione

Raw materials: ninhydrin, 4-(4-methoxyphenyl)-semicarbazide hydrochloride

Yield: 80%, M.P. 218° C.; IR: $\upsilon$ NH=3280 and 3220 $cm^{-1}$, $\upsilon$ CO=1720 and 1665 cm-1.

Recrystallisation solvent: isopropanol

EXAMPLE 9

2-[4-(2,5,-dimethoxyphenyl)-semicarbazono]indan-1,3-dione

Raw materials: ninhydrin, 4-(2,5-dimethoxyphenyl)-semicarbazide hydrochloride

Yield: 75%; M.P. 222° C.; IR: $\upsilon$ NH=3340 and 3200 $cm^{-1}$; $\upsilon$ CO=1730 and 1690 $cm^{-1}$ Recrystallisation solvent: isopropanol

EXAMPLE 10

2-[4-(3,5-dimethoxyphenyl)-semicarbazono]indan-1,3-dione

Raw materials: ninhydrin, 4-(3,5-dimethoxyphenyl)-semicarbazide hydrochloride

Yield: 80%; M.P. 234° C.; IR: $\upsilon$ NH=3380 and 3230 $cm^{-1}$; $\upsilon$ CO=1730 and 1690 $cm^{-1}$ Recrystallisation solvent: ethyl acetate

EXAMPLE 11

2-[4-(3,4-dimethoxyphenyl)-semicarbazono]indan-1,3-dione

Raw materials: ninhydrin, 4-(3,4-dimethoxyphenyl)-semicarbazide hydrochloride

Yield: 70%; M.P. 210° C.; IR: $\upsilon$ NH=3400 and 3260 $cm^{-1}$; $\upsilon$ CO=1720 and 1670 $cm^{-1}$ Recrystallisation solvent: ethyl acetate

EXAMPLE 12

2-[4-(2-chloro-5-methoxyphenyl)-semicarbazono]indan-1,3-dione

Raw materials: ninhydrin, 4-(2-chloro-5-methoxyphenyl)-semicarbazide hydrochloride Yield: 80%; M.P. 228° C.; IR: $\upsilon$ NH=3330 and 3260 $cm^{-1}$; $\upsilon$ CO=1730 and 1680 $cm^{-1}$ Recrystallisation solvent: ethyl acetate

EXAMPLE 13

2-(4,4-diphenylsemicarbazono)-indan-1,3-dione

Raw materials: ninhydrin, 4,4-diphenyl semicarbazide hydrochloride

Yield: 45%; M.P. 256° C.; IR: $\nu$ NH=3200 cm$^{-1}$, $\nu$ CO=1720, 1700 and 1670 cm$^{-1}$ Recrystallisation solvent: methanol

EXAMPLE 14

2-[4-(2-methylphenyl)-semicarbazono]indan-1,3-dione

Raw materials: ninhydrin, 4-(2-methylphenyl)-semicarbazide hydrochloride

Yield: 60%; M.P. 192° C.; IR: $\nu$ NH=3340 and 3210 cm$^{-1}$; $\nu$ CO=1720 and 1675 cm$^{-1}$ Recrystallisation solvent: ethanol

EXAMPLE 15

2-[4-(3-methylphenyl)-semicarbazon]indan-1,3-dione, monohydrate

Raw materials: ninhydrin, 4-(3-methylphenyl)-semicarbazide hydrochloride

Yield: 95%; M.P. 128° C.; IR: $\nu$ NH=3260 and 3240 cm$^{-1}$; $\nu$ CO=1720 and 1670 cm$^{-1}$ Recrystallisation solvent: methanol

EXAMPLE 16

2-[4-(4-methylphenyl)-semicarbazono]indan-1,3-dione

Raw materials: ninhydrin, 4-(4-methylphenyl)-semicarbazide hydrochloride

Yield: 74%; M.P. 208° C.; IR: $\nu$ NH=3380 and 3200 cm$^{-1}$; $\nu$ CO=1720 and 1670 cm$^{-1}$ Recrystallisation solvent: ethyl ether

EXAMPLE 17

2-[4-(4-propylphenyl)-semicarbazono]indan-1,3-dione

Raw materials: ninhydrin, 4-(4-propylphenyl)-semicarbazide hydrochloride

Yield: 74%; M.P. 166° C.; IR: $\nu$ NH=3215 cm$^{-1}$; $\nu$ CO=1710 and 1680 cm$^{-1}$ Recrystallisation solvent: ethanol

EXAMPLE 18

2-[4-(4-tert-butylphenyl)-semicarbazono]indan-1,3-dione

Raw materials: ninhydrin, 4-(4-tert-butylphenyl)-semicarbazide hydrochloride

Yield: 40%; M.P. 258° C.; IR: $\nu$ NH=3360 and 3200 cm$^{-1}$; $\nu$ CO=1710 and 1670 cm$^{-1}$ Recrystallisation solvent: ethanol

EXAMPLE 19

2-[4-(2-chlorophenyl)-semicarbazono]indan-1,3-dione

Raw materials: ninhydrin, 4-(2-chlorophenyl)-semicarbazide hydrochloride

Yield: 75%; M.P. 208° C.; IR: $\nu$ NH=3330 and 3220 cm$^{-1}$; $\nu$ CO=1710 and 1670 cm$^{-1}$ Recrystallisation solvent: ethyl acetate

EXAMPLE 20

2-[4-(2-chloro-6-methylphenyl)-semicarbazono]indan-1,3-dione

Raw materials: ninhydrin, 4-(2-chloro-6-methylphenyl)-semicarbazide hydrochloride Yield: 75%; M.P. 228° C.; IR: $\nu$ NH=3320 and 3200 cm$^{-1}$; $\nu$ CO=1710 and 1670 cm$^{-1}$ Recrystallisation solvent: ethanol

EXAMPLE 21

2-[4-(4-chlorophenyl)-semicarbazono]indan-1,3-dione

Raw materials: ninhydrin, 4-(4-chlorophenyl)-semicarbazide hydrochloride

Yield: 75%; M.P. 234° C.; IR: $\nu$ NH=3300 and 3280 cm$^{-1}$; $\nu$ CO=1730 and 1680 cm$^{-1}$ Recrystallisation solvent: isopropanol

EXAMPLE 22

2-[4-(2,5-diethoxyphenyl)-semicarbazono]indan-1,3-dione

Raw materials: ninhydrin, 4-(2,5-diethoxyphenyl)-semicarbazide hydrochloride

Yield: 40%; M.P. 226° C.; IR: $\nu$ NH=3340 cm$^{-1}$; $\nu$ CO=1720 and 1675 cm$^{-1}$ Recrystallisation solvent: isopropanol

EXAMPLE 23

2-[4-ethylthiosemicarbazono)-indan-1,3-dione

Raw materials: ninhydrin, 4-ethyl thiosemicarbazide hydrochloride

Yield: 30%; M.P. 212° C.; IR: $\nu$ NH=3340 and 3240 cm$^{-1}$; $\nu$ CO=1720 and 1670 cm$^{-1}$ Recrystallisation solvent: ethanol

EXAMPLE 24

2-(4-methylthiosemicarbazonol-indan-1,3-dione

Raw materials: ninhydrin, 4-methyl thiosemicarbazide hydrochloride

Yield: 70%; M.P. 234° C.; IR: $\nu$ NH=3200 cm$^{-1}$; $\nu$ CO=1710 and 1670 cm$^{-1}$ Recrystallisation solvent: a (V/V) mixture of methanol and ethyl acetate

EXAMPLE 25

2-[4-(4-ethylphenyl)-semicarbazono]indan-1,3-dione

Raw materials: ninhydrin, 4-(4-ethylphenyl)-semicarbazide hydrochloride

Yield: 60%; M.P. 180° C.; IR: $\nu$ NH=3330 and 3220 cm$^{-1}$; $\nu$ CO=1715 and 1670 cm$^{-1}$ Recrystallisation solvent: ethanol

EXAMPLE 26

2-[4-(3-ethoxyphenyl)-semicarbazono]indan-1,3-dione

Raw materials: ninhydrin, 4-(3-ethoxyphenyl)-semicarbazide hydrochloride

Yield: 85%; M.P. 164° C.; IR: $\nu$ NH=3240 cm$^{-1}$; $\nu$ CO=1730 and 1680 cm$^{-1}$ Recrystallisation solvent: methanol

EXAMPLE 27

2-[4-(4-ethoxyphenyl)-semicarbazono]indan-1,3-dione

Raw materials: ninhydrin, 4-(4-ethoxyphenyl)-semicarbazide hydrochloride

Yield: 70%; M.P. 200° C.; IR: $\nu$ NH=3300 and 3210 cm$^{-1}$; $\nu$ CO=1720 and 1670 cm$^{-1}$ Recrystallisation solvent: ethyl acetate

EXAMPLE 28

2-[4-(2,4-dichlorophenyl)-semicarbazono]indan-1,3-dione

Raw materials: ninhydrin, 4-(2,4-dichlorophenyl)-semicarbazide hydrochloride

Yield: 35%; M.P. 226° C.; IR: $\nu$ NH=3315 and 3210 cm$^{-1}$; $\nu$ CO=1710 and 1670 cm$^{-1}$ Recrystallisation solvent: isopropanol

EXAMPLE 29

2-[4-(3,4-methylenedioxyphenyl)-semicarbazono]indan-1,3-dione

Raw materials: ninhydrin, 4-(3,4-methylenedioxyphenyl)-semicarbazide hydrochloride Yield: 70%; M.P. 228° C.; IR: $\nu$ NH=3250 cm$^{-1}$; $\nu$ CO=1715 and 1670 cm$^{-1}$ Recrystallisation solvent: ethyl acetate

EXAMPLE 30

2-[4-(2-fluorophenyl)-semicarbazono]indan-1,3-dione

Raw materials: ninhydrin, 4-(2-fluorophenyl)-semicarbazide hydrochloride

Yield: 80%; M.P. 195° C.; IR: $\nu$ NH=3310 and 3210 cm$^{-1}$; $\nu$ CO=1720, 1700 and 1665 cm$^{-1}$ Recrystallisation solvent: methanol/ethyl acetate (V/V)

EXAMPLE 31

2-[4-(3-fluorophenyl)-semicarbazono]indan=1,3-dione

Raw materials: ninhydrin, 4-(3-fluorophenyl)-semicarbazide hydrochloride

Yield: 90%; M.P. 222° C.; IR: $\nu$ NH=3360 and 3230 cm$^{-1}$; $\nu$ CO=1740 and 1695 cm$^{-1}$ Recrystallisation solvent: ethyl acetate

EXAMPLE 32

2-[4-(4-fluorophenyl)-semicarbazono]indan-1,3-dione

Raw materials: ninhydrin, 4-(4-fluorophenyl)-semicarbazide hydrochloride

Yield: 80%; M.P. 230° C.; IR: $\nu$ NH=3320 and 3200 cm$^{-1}$; $\nu$ CO=1710 and 1660 cm$^{-1}$ Recrystallisation solvent: ethyl acetate

EXAMPLE 33

2-[4-(2-bromophenyl)-semicarbazono]indan-1,3-dione

Raw materials: ninhydrin, 4-(2-bromophenyl)-semicarbazide hydrochloride

Yield: 80%; M.P. 235° C.; IR: $\nu$ NH=3320 and 3220 cm$^{-1}$; $\nu$ CO=1715 and 1680 cm$^{-1}$ Recrystallisation solvent: ethyl acetate

EXAMPLE 34

2-[4-(4-bromophenyl)-semicarbazono]indan-1,3-dione

Raw materials: ninhydrin, 4-(4-bromophenyl)-semicarbazide hydrochloride

Yield: 80%; M.P. 236° C.; IR: $\nu$ NH=3230 cm$^{-1}$; $\nu$ CO=1750, 1730 and 1690 cm$^{-1}$ Recrystallisation solvent: ethyl acetate

EXAMPLE 35

2-[4-(2-hydroxyethyl)-semicarbazono]-1,3-dione

Raw materials: ninhydrin, 4-(2-hydroxyethyl)-semicarbazide hydrochloride

Yield: 70%; M.P. 247° C.; IR: $\nu$ OH/NH=3360, 3240 and 3220 cm$^{-1}$; $\nu$ CO=1710 and 1680 cm$^{-1}$ Recrystallisation solvent: methanol

EXAMPLE 36

2-[4-(2-acetoxyphenyl)-semicarbazono]indan-1,3-dione

Two drops of concentrated sulphuric acid were added to a solution of 1 g (0.003 mol) of 2-[4-(2-hydroxyphenyl)-semicarbazono]indan-1,3-dione (example 4) in 10 ml acetic anhydride.

The reaction mixture was agitated at ambient temperature for 10 minutes, then poured into ice water. The resulting yellow precipitate was dried on suction pump, repeatedly washed with water, dried and recrystallised from acetonitrile.

Yield: 45%; M.P. 242° C.; IR: $\nu$ NH=3320 and 3180 cm$^{-1}$; $\nu$ CO=1740, 1715 and 1675 cm$^{-1}$

EXAMPLE 37

5-methoxy-2-(4-phenylsemicarbazono)-indan-1,3-dione

Raw materials: 5-methoxyindan-1,2,3-trione, monohydrate, 4-phenyl semicarbazide hydrochloride Yield: 61%; M.P. 230° C.; IR: $\nu$ NH=3250 cm$^{-1}$; $\nu$ CO=1720 and 1680 cm$^{-1}$ Recrystallisation solvent: ethanol

EXAMPLE 38

5-methoxy-2-(4-phenylthiosemicarbazono)-indan-1,3-dione

Raw materials: 5-methoxyindan-1,2,3-trione, monohydrate, 4-phenyl thiosemicarbazide hydrochloride Yield: 48%; M.P. 149° C.; IR: υ NH=3260 cm$^{-1}$, υ CO=1720 and 1680 cm$^{-1}$ Recrystallisation solvent: ethanol

EXAMPLE 39

5-methoxy-2-semicarbazono-indan-1,3-dione

Raw materials: 5-methoxyindan-1,2,3-trione, monohydrate, semicarbazide hydrochloride Yield: 86%; M.P.>265° C.; IR: υ NH=3320 and 3220 cm$^{-1}$, υ CO=1720 and 1680 cm$^{-1}$ Recrystallisation solvent: mixture (V/V) of ethanol and ethyl acetate

EXAMPLE 40

5-methoxy-2-[4-(2-hydroxyphenyl)-semicarbazono]indan-1,3-dione

Raw materials: 5-methoxyindan-1,2,3-trione, monohydrate, 4-(2-hydroxyphenyl)-semicarbazide hydrochloride; reflux for 5 hours Yield: 60%; M.P. 262° C.; IR: υ OH=3400 cm$^{-1}$, υ NH=3300 cm$^{-1}$, υ CO=1750, 1700 and 1620 cm$^{-1}$ Precipitate washed in ether.

EXAMPLE 41

5-methoxy-2-thiosemicarbazono-indan-1,3-dione

Raw materials: 5-methoxyindan-1,2,3-trione, monohydrate, thiosemicarbazide hydrochloride Yield: 43%; M.P.>265° C.; IR: υ NH=3220 and 3120 cm$^{-1}$, υ CO=1710 and 1655 cm$^{-1}$ Recrystallisation solvent: ethanol

EXAMPLE 42

5-hydroxy-2-(4-phenylsemicarbazono),indan-1,3-dione

Raw materials: 5-hydroxyindan-1,2,3-trione, monohydrate, 4-phenyl semicarbazide hydrochloride; reflux for 4 hours Yield: 70%; M.P. 265° C.; IR: υ OH=3400 cm$^{-1}$, υ NH=3240 and 3220 cm$^{-1}$, υ CO=1680 cm$^{-1}$ Recrystallisation solvent: acetonitrile

EXAMPLE 43

5-hydroxy-2-semicarbazono-indan-1,3-dione

Raw materials: 5-hydroxyindan-1,2,3-trione, monohydrate, semicarbazide hydrochloride, reflux for 4 hours.

Yield: 50%; M.P.>265° C.; IR: υ OH/NH$_2$=3420 cm$^{-1}$, υ CO=1720 and 1660 cm$^{-1}$ Recrystallisation solvent: ethanol

EXAMPLE 44

5-hydroxy-2-(4-phenylthiosemicarbazono)-indan-1,3-dione

Raw materials: 5-hydroxyindan-1,2,3-trione, monohydrate, 4-phenyl thiosemicarbazide hydrochloride, reflux for 2 hours.

Yield: 45%; M.P.>265° C.; IR: υ OH=3400 cm$^{-1}$, υ NH=3300 and 3120 cm$^{-1}$, υ CO=1710 and 1675 cm$^{-1}$ Recrystallisation solvent: mixture (V/V) of ethyl acetate and petroleum ether

EXAMPLE 45

5-hydroxy-2-thiosemicarbazono-indan-1,3-dione

Raw materials: 5-hydroxyindan-1,2,3-trione, monohydrate, thiosemicarbazide hydrochloride, reflux for 2 hours.

Yield: 78%; M.P.>265° C.; IR: υ OH=3420 cm$^{-1}$, υ NH=3300 and 3120 cm$^{-1}$, υ CO=1710 and 1680 cm$^{-1}$ Recrystallisation solvent: mixture (V/V) of ethyl acetate and petroleum ether

EXAMPLE 46

5,6-dimethoxy-2-semicarbazono-indan-1,3-dione, monohydrate

Raw materials: 5,6-dimethoxyindan-1,2,3-trione, monohydrate, semicarbazide hydrochloride Yield: 60%; M.P.>265° C.; IR: υ NH=3420 and 3300 cm$^{-1}$; υ CO=1730 and 1680 cm$^{-1}$ Recrystallisation solvent: methanol

EXAMPLE 47

5,6-dimethoxy-2-(4-phenyl semicarbazono)-indan-1,3-dione, monohydrate

Raw materials: 5,6-dimethoxyindan-1,2,3-trione, monohydrate, 4-phenyl semicarbazide hydrochloride Yield: 80%; M.P.>265° C.; IR: υ NH=3240 cm$^{-1}$; υ CO=1730, 1710 and 1670 cm$^{-1}$ Recrystallisation solvent: methanol

EXAMPLE 48

2-[4-(3-trifluoromethylphenyl)-semicarbazono]indan-1,3-dione

Raw materials: ninhydrin, 4-(3-trifluoromethyl phenyl)-semicarbazide hydrochloride Yield: 70%; M.P. 230° C.; IR: υ NH=3360 and 3180 cm$^{-1}$; υ CO=1730 and 1680 cm$^{-1}$ Recrystallisation solvent: ethyl acetate

EXAMPLE 49

2-[4-(2-trifluoromethylphenyl)-semicarbazono]indan-1,3-dione

Raw materials: ninhydrin, 4-(2-trifluoromethyl phenyl)-semicarbazide hydrochloride Yield: 70%; M.P. 160° C.; IR: υ=3360 and 3180 cm$^{-1}$; υ CO=1740 and 1680 cm$^{-1}$ Recrystallisation solvent: a mixture (V/V) of ether and isopropanol

EXAMPLE 50

2-[4-(3-bromophenyl)-thiosemicarbazono]indan-1,3-dione

Raw materials: ninhydrin, 4-(3-trifluoromethyl phenyl)-semicarbazide hydrochloride Yield: 75%; M.P. 180° C.; IR: υ NH=3360 and 3180 cm$^{-1}$; υ CO=1730 and 1680 cm$^{-1}$ Recrystallisation solvent: methanol

EXAMPLE 51

2-[4-(4-bromophenyl)-thiosemicarbazono]indan-1,3-dione

Raw materials: ninhydrin, 4-(4-bromophenyl)-thiosemicarbazide hydrochloride

Yield: 50%; M.P. 230° C.; IR: $\upsilon$ NH=3340 cm$^{-1}$; $\upsilon$ CO=1730 and 1700 cm$^{-1}$

EXAMPLE 52

2-[4-(pyridin-4-yl) semicarbazono]indan-1,3-dione 70 mmols of 4-pyridyl semicarbazide in suspension in 100 ml ethanol were added at ambient temperature to 70 mmols of 2,2-dihydroxy-1,3-dioxo-2H-indene in solution in 100 ml ethanol. The reaction mixture, which became yellow, was kept agitated at ambient temperature for 24 hours. The resulting precipitate was filtered over fritted glass and washed in ether and in pentane. The crystals, which were yellow, were purified on a silica column, average pressure, and recrystallised. They were dried overnight in vacuo at 50° C.

Yield: 74%; M.P.>260° C.; IR (KBr): $\upsilon$ NH=3300 cm$^{-1}$; $\upsilon$ CO=1730 and 1670 cm$^{-1}$ NMR of $^1$H (200 MHz, DMSOd$_6$): $\delta$ (ppm) 10.65 (1s, 1H, NH); 8.45 (d, 2H, H-2', H6', J2'-3' and 5'-6'=6 Hz); 8.00 (s, 4H, H-4, H-5, H-6, H-7); 7.65 (d, 2H, H-3', H-5', J2'-3' and 5'-6'=6 Hz)

Recrystallisation solvent: ethyl acetate

EXAMPLE 53

2-[4-(2,4-diflourophenyl)semicarbazono]indan-1,3-dione

Raw materials: 2,2-dihydroxy-1,3-dioxo-2H-indene; 4-(2,4-difluorophenyl) semicarbazide, hydrochloride Yield: 80%; M.P. 231° C.; IR (KBr): $\upsilon$ NH=3300 and 3220 cm$^{-1}$; $\upsilon$ C=O=1725 and 1700 cm$^{-1}$ NMR of $^1$H (200 MHz, DMSO d$_6$): $\delta$ (ppm) 13.53 (1s, 1H, NH); 12.21 (1s, 1H, NH); 7.98 (s, 4H, H-4, H-5, H-6, H-7); 7.93 (m, 1H, H-3'); 7.30 (m, 1H, H-5'); 7.10 (s, 1H, H-6')

Recrystallisation solvent: ethyl acetate

EXAMPLE 54

2-[4-(2,6-difluorophenyl)semicarbazono]indan-1,3-dione

Raw materials: 2,2-dihydroxy-1,3-dioxo-2H-indene; 4-(2,6-difluorophenyl)semicarbazide, hydrochloride Yield: 74%; M.P. 268° C.; IR (KBr): $\upsilon$ NH=3300 and 3220 cm$^{-1}$; $\upsilon$ CO=1725 and 1700 cm$^{-1}$ NMR of $^1$H (200 MHz, DMSO d$_6$): $\delta$ (ppm) 12.47 (1s, 1H, NH); 9.98 (1s, 1H, NH); 8.00 (s, 4H, H-4, H-5, H-6, H-7); 7.49 (m 1H, H-4'); 7.27 (t 2H, H-3', H-5', JH5'-4'= JH3'-4'=7.91 Hz)

Recrystallisation solvent: ethyl alcohol

EXAMPLE 55

2-[4-(4-trifluoromethylphenyl)semicarbazono]indan-1,3-dione

Raw materials: 2,2-dihydroxy-1,3-dioxo-2H-indene; 4-(4-trifluoromethylphenyl)semicarbazide, hydrochloride Yield: 90%; M.P. 254° C. (decomposition); IR (KBr): $\upsilon$ NH=3280 and 3220 cm$^{-1}$; $\upsilon$ CO=1740 and 1700 cm$^{-1}$ NMR of $^1$H (200 MHz, DMSO d$_6$): $\delta$ (ppm) 12.56 (1s, 1H, NH ); 10.73 (1s, 1H, NH ); 8.00 ( s, 4H, H-4, H-5, H-6, H-7); 7.80 (d, 2H, H-3', H-5', JH3'-2' and 6'-5'=8.4 Hz) 7.72 (d, 2H, H-2', H-6', JH3'-2' and 6'-5'=8.4 Hz)

Recrystallisation solvent: dichloromethane

EXAMPLE 56

2-[4-(2,4-difluoro-6-ethoxyphenyl)semicarbazono]indan-1,3-dione

Raw materials: 2,2-dihydroxy-1,3-dioxo-2H-indene; 4-(2,4-difluoro-6-ethoxyphenyl)semicarbazide, hydrochloride Yield: 79%; M.P. 203° C.; IR (KBr): $\upsilon$ NH=3240 cm$^{-1}$; $\upsilon$ CO=1730, 1710 and 1670 cm$^{-1}$ NMR of $^1$H (200 MHz, DMSO d$_6$); $\delta$ (ppm) 13.13 (s, 1H, NH); 9.28 (s, 1H, NH); 7.94 (s, 4H, H-4, H-5, H-6, H-7); 7.31 (m, 1H, H-3'); 7.19 (m, 1H, H-5'); 4.20 (q, 2H, CH$_2$, J=8 Hz); 1.32 (t, 3H, CH$_3$, J=8 Hz)

Recrystallisation solvent: dichloromethane

EXAMPLE 57

2-[4-(4-fluorophenyl)thiosemicarbazono]indan-1,3-dione

Raw materials: 2,2-dihydroxy-1,3-dioxo-2H-indene; 4-(4-fluorophenyl)thiosemicarbazide, hydrochloride Yield: 60%; M.P. 209° C.; IR (KBr): $\upsilon$ NH=3270 and 3210 cm$^{-1}$; $\upsilon$ CO=1725 and 1680 cm$^{-1}$ NMR of $^1$H (200 MHz, DMSO d$_6$): $\delta$ (ppm) 12.85 (1s, 1H, NH); 11.24 (1s, 1H, NH); 8.00 (s, 4H, H-4, H-5, H-6, H-7); 7.60 (m, 2H, H-3', H-5'); 7.24 (t, 2H, H-2', H-6', JH2'-3' and 5'-6'=8.9 Hz)

Recrystallisation solvent: dichloromethane

EXAMPLE 58

2-[4-(2-fluorophenyl)thiosemicarbazono]indan-1,3-dione

Raw materials: 2,2-dihydroxy-1,3-dioxo-2H-indene; (2-fluorophenyl)thiosemicarbazide, hydrochloride Yield: 77%; M.P. 224° C.; IR (KBr): $\upsilon$ NH=3240 and 3200 cm$^{-1}$; $\upsilon$ CO=1720 and 1680 cm$^{-1}$ NMR of $^1$H (200 MHz, DMSO d$_6$): $\delta$ (ppm) 12.89 (1s, 1H, NH): 11.00 (1s, 1H, NH); 8.00 (s, 4H, H-4, H-5, H-6, H-7); 7.49 (m, 1H, H-3'); 7.34 (m, 3H, H-4', H-5', H-6').

Recrystallisation solvent: ethyl ether

E. Preparation of formula (If) compounds

METHOD 5

40 ml of an aqueous solution containing 5.6 mmols of hydrazinocarbonyl hydrazine of hydrazinothiocarbonyl hydrazine was added to a solution of 5.6 mmols of 2,2-dihydroxy-1,3-dioxo-2H-indene in 30 ml ethanol.

The reaction mixture was agitated at ambient temperature for 7 hours and the resulting white precipitate was dried on suction pump, washed in ethanol and dried. The precipitate was then suspended in 20 ml ethanol, followed by addition of two drops of concentrated hydrochloric acid. The mixture was refluxed for 30 minutes and the resulting yellow-orange product was precipitated, dried and recrystallised.

EXAMPLE 59

2-(phenylhydrazinocarbonylhydrazono)indan-1,3-dione

Raw materials: 2,2-dihydroxy-1,3-dioxo-2H-indene; phenyl hydrazinocarbonyl hydrazine Yield: 98%; M.P. 245° C.; IR (KBr): $\upsilon$ NH=3320 cm$^{-1}$; $\upsilon$ CO=1740, 1720 and 1680 cm$^{-1}$ NMR of $^1$H (200 MHz, DMSO d$_6$): δ (ppm) 13.25 (s, 1H, NH); 9.37 (s, 1H, NH); 8.17 (s, 1H, NH); 7.95 (s, 4H, H-4, H-5, H-6, H-7); 7.23 (m, 2H, H-2', H-6'); 7.30 (m, 3H, H-3', H-4', H-5')

Recrystallisation solvent: acetone

EXAMPLE 60

2-[(4-fluorophenyl)hydrazinocarbonylhydrazino]indan-1,4-dione

Raw materials: 2,2-dihydroxy-1,3-dioxo-2H-indene. (4-fluorophenyl)hydrazinocarbonyl hydrazine Yield: 67%; M.P. 250° C.; IR (KBr): $\upsilon$ NH=3240 and 3320 cm$^{-1}$; $\upsilon$ CO=1740 and 1700 cm$^{-1}$ NMR of $^1$H (200 MHz, DMSO d$_6$): δ (ppm) 13.25 (1s, 1H, NH); 9.43 (1s, 1H, NH); 8.20 (1s, 1H, NH); 7.95 (s, 4H, H-4, H-5, H-6, H-7); 7.10 (m, 2H, H-3', H-5'); 6.88 (m, 2H, H-2', H-6')

Recrystallisation solvent: ethanol/acetone 50/50%

F. Preparation of formula (Ig) compounds

METHOD 6

10 ml of an aqueous solution containing 30 mmols of (arylimino)methyl thiohydrazine were added to a solution of 30 mmols of 2,2-dihydroxy-1,3-dioxo-2H-indene in 70 ml ethanol.

The reaction mixture was brought to 60° C. for 30 minutes and the resulting maroon-orange precipitate was dried on suction pump when hot, dried and recrystallised.

EXAMPLE 61

2-[(phenylimino)methylthiohydrazono]indan-1,3,-dione

Raw materials: 2,2-dihydroxy-1,3-dioxo-2H-indene (phenylimino)methylthiohydrazine Yield: 40%; M.P. 200° C.; IR (KBr): $\upsilon$ NH=3200 cm$^{-1}$; $\upsilon$ CO=1720 and 1690 cm$^{-1}$ NMR of $^1$H (200 MHz, DMSO d$_6$): δ (ppm) 12.75 (1s, ½H, NH); 9.63 (1s, ½H, NH); 7.98 (d, 1H, H-2' or H-6', JH2'-3'=7.4 Hz); 7.92 (s, 4H, H-4, H-5, H-6, H-7); 7.44 (m, 2H, H-3', H-5'); 7.21 (t, 1H, H-4', JH4'-5'=7.4); 6.97 (d, 1H, H-2' or H-6', JH2'-3'=7.4 Hz); 2.50 (s, 3H, CH$_3$)

Recrystallisation solvent: Ethyl acetate

EXAMPLE 62

2-[(4-fluorophenylimino)methylthiohydrazono]indan-1,3-dione

Raw materials: 2,2-dihydroxy-1,3-dioxo-2H-indene (4-fluorophenylimino)methylthiohydrazine Yield: 50%; M.P.>260° C.; IR (KBr): $\upsilon$ NH=3180 cm$^{-1}$; $\upsilon$ CO=1740 and 1680 cm$^{-1}$ NMR of $^1$H (200 MHz, DMSO d$_6$): δ (ppm) 12.86 (s, ½H, NH ); 9.78 (s, ½H, NH ); 8.14 (d, 1H, H-2' or H-6', JH2'-3'=7.4 Hz); 8.00 (s, 4H, H-4, H-5, H-6, H-7); 7.37 (m, 2H, H-3', H-5'); 7.13 (d, 1H, H-2' or H-6', JH2'-3'=7.4 Hz); 2.61 (s, 3H, CH$_3$)

Recrystallisation solvent: acetone

G. Preparation of formula (Ii)–(Ik) compounds

METHOD 7

EXAMPLE 63

1,2-(4-phenylsemicarbazono)-3-indanone

Raw materials: Ninhydrin, 4-phenyl semicarbazide hydrochloride

Yield: 70%; M.P.>260° C.; IR: $\upsilon$ NH=3360, 3325 and 3300 cm$^{-1}$; $\upsilon$ CO=1700 and 1675 cm$^{-1}$ Precipitate washed in ethanol

EXAMPLE 64

1-oximino-2-(4-phenylsemicarbazono)-3-indanone 0.01 mol of hydroxylamine hydrochloride and 0.01 mol sodium acetate in solution in 20 ml water were added to a solution of 0.01 mol of 2-(4-phenyl semicarbazono)-indan-1,3-dione in 150 ml ethanol. The reaction mixture was refluxed for 1 hour, then the ethanol was eliminated at reduced pressure. The resulting crystals were dried on suction pump, washed in water, dried and recrystallised from isopropanol.

Yield: 70%; M.P. 240° C.; IR: $\upsilon$ OH=3400 cm$^{-1}$; $\upsilon$ NH=3300 and 3240 cm$^{-1}$, $\upsilon$ CO=1710 cm$^{-1}$ H. Preparation of formula (Il) and (Im) compounds

METHOD 9

EXAMPLE 65

1,3-dioximino-2-(4-phenylsemicarbazono)-indan 0.02 mol of hydroxylamine hydrochloride and 0.01 mol sodium acetate in solution in 20 ml water were added to a solution of 0.01 mol of 2-(4-phenyl semicarbazono)indan-1,3-dione in 150 ml ethanol. The reaction mixture was refluxed for 1 hour, then the ethanol was eliminated at reduced pressure. The resulting crystals were dried on suction pump, washed in water, dried and recrystallised from ethyl acetate.

Yield: 65%; M.P.>265° C.; IR: $\upsilon$ OH=3450 m$^{-1}$, $\upsilon$ NH=3180 cm$^{-1}$, $\upsilon$ CO=1680 cm$^{-1}$ Note that the infrared spectra hereinafter were determined using KBr pellets.

The following are the NMR spectra of the compounds in the previous examples. These spectra were determined on an NMR apparatus, 200 MHz, in solution in DMSO (D6). They are described in accordance with the following protocol:

shift (δ) in ppm, shape of signal, number of protons, nature of protons, coupling constants if applicable.

The aromatic protons on indan were numbered as follows:

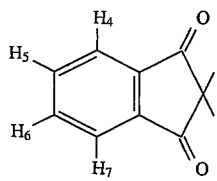

In the case where R and $R_1$ comprise a heterocyclic ring or form a group containing a heterocyclic ring, the protons in the ring are numbered from the heteroatom in the direction of the bond to the main substrate.

NMR spectra

EXAMPLE A

5-Hydroxyindane-1,3-dione 7.78 (d, 1H, H-7, J H6–7=8.3 Hz) 7.26 (d ,1H, H-6, J H6–7=8.3 Hz) 7.11 (1s, 1H, H-4) 3.25 (s, 3H, CH2)

EXAMPLE B

2-Bromo-5-hydroxyindane-1,3-dione 11,55 (1s, OH) 7.90 (dd, 1H, H-6, J H6-4=2.93 Hz; J H6–7=8.3 Hz) 7.39 (d, 1H, H-7, J H6–7=8.3 Hz) 7.21 (s, 1H, H-4) 5.50 (s, 1H, H2)

EXAMPLE C

5-Hydroxyindane-1,2,3-trione, monohydrate 11.50(1s, 1H, OH) 7.90 (d, 1H, H7, J H6–7=5.9 Hz) 7.40 (m, 2H, H4, H6)

EXAMPLE D 5,6-Dimethoxyindane-1,2,3-trione, monohydrate 7.40 (1s, 2H, H-4, H-7) 4.03 (s, 6H, 2CH3O)

EXAMPLE E

6-Hydroxy-5-methoxyindane-1,2,3-trione, monohydrate 11.21 (1s, 1H, OH) 7.28 (m, 2H, H-4, H-7) 4.03 (s, 6H, 2CH3O)

EXAMPLE F 2-oximino-5-hydroxyindane-1,3-dione 9.16 (1s, 1H, OH) 7.83 (dd, 1H, H6, JH6–7=9.0 Hz and JH4–6=3.0 Hz) 7.21 (m, 2H, H7, H4)

EXAMPLE 1

2-Hydroxy-2-[4-2-hydroxyphenyl)-semicarbazido]indane-1,3-dione 9.55 (1s, 1H, NH) 8.27 (s, 1H, OH) 8.00 (s, 4H, H-4, H-5, H-6, H-7) 7.90 (m, 2H, NH, H-3') 7.13 (1s, 1H, OH) 6.71 (m, 3H, H-4', H-5', H-6') 6.30 (1s, 1H, NH)

EXAMPLE 2

2-semicarbazono-indane-1,3-dione 12.55 (s, 1H,NH) 7.95 (s, 4H, H-4, H-5, H-6, H-7) 7.41 (s, 2H, NH2)

EXAMPLE 3

2-(4-Phenylsemicarbazono)-indane-1,3-dione 12.55 (s, 1H, NH) 10.35 (s, 1H, NH) 8.00 (s, 4H, H-4, H-5, H-6, H-7) 7.65 (d, 2H, H-2', H-6', J H2'–3' & 5'–6'=8.2 Hz) 7.35 (dd, 2H, H-3', H-5', J H2'–3' & 5'–6'=8.2 Hz) 7.10 (m, 1H, H-4')

EXAMPLE 4

2-[4-(2-hydroxyphenyl)-semicarbazono]indane-1,3-dione 12.55 (s, 1H, NH) 10.18 (s, 1H, OH) 9.64 (s, 1H, NH) 7.97 (s, 5H. H-4, H-5, H-6, H-7, H-6') 6.92 (m, 3H, H-3', H-4', H-5')

EXAMPLE 5

2-(4-Phenylthiosemicarbazono)indane-1,3-dione 12.50 (1s, 1H, NH) 10.35 (1s, 1H, NH) 7.95 (s, 4H, H-4, H-5, H-6, H-7) 7.58 (d, 2H, H-2', H-6', J H2'–3' & 5'–6'=8.3 Hz) 7.34 (dd, 2H, H-3', H-5', J H2'–3' & 5'–6'=8.3 Hz) 7.07 (dd, 1H, H-4', J H4'–5' & 3'–4'=8.3 Hz)

EXAMPLE 6

2-[4-(2-Methoxyphenyl)-semicarbazono]indane-1,3-dione 12.57 (s, 1H, NH) 9.69 (s, 1H, NH) 8.03 (m, 1H, H-6') 7.95 (s, 4H, H-4, H-5, H-6, H-7) 7.06 (m, 2H, H-3', H-5') 6.97 (m, 1H, H-4') 3.89 (s, 3H, CH3)

EXAMPLE 7

2-[4-(3-Methoxyphenyl)-semicarbazono]indane-1,3-dione 12.48 (1s, 1H, NH) 10.32 (1s, 1H, NH) 7.96 (s, 4H, H-4, H-5, H-6, H-7) 7.22 (m, 3H, H-4', H-5', H-6') 6.65 (d, 1H, H-3', J H3'–4'=7.8 Hz) 3.75 (s, 3H, CH3O)

EXAMPLE 8

2-[4-(4-Methoxyphenyl)-semicarbazono]indane-1,3-dione, monohydrate 12.46 (1s, 1H, NH) 10.22 (1s, 1H, NH) 7.96 (s, 4H, H-4, H-5, H-6, H-7) 7.50 (d, 2H, H-2', H-6', J H2'–3' & 5'–6'=8.8 Hz) 6.92 (d, 2H, H-3', H-5', J H2'–3' & 5'–6'=8.8 Hz) 3.73 (s, 3H, CH3O)

EXAMPLE 9

2-[4-(2,5-Dimethoxyphenyl)-semicarbazono]indane-1,3-dione 12.54 (1s, 1H, NH) 9.68 (1s, 1H, NH) 7.96 (s, 4H, H-4, H-5, H-6, H-7) 7.73 (m, 1H, H-6') 6.98 (d, 1H, H-3', J H3'–4'=8.3 Hz) 6.63 (dd, 1H, H-4', J H3'–4'=8.3 Hz) 3.83 (s, 3H, CH3O) 3.70 (s, 3H, CH3O)

EXAMPLE 10

2-[4-(3,5-Dimethoxyphenyl)-semicarbazono] indane-1,3-dione 12.50 (s, 1H, NH) 9.75 (s, 1H, NH) 8.00 (s, 4H, H-4, H-5, H-6, H-7) 6.85 (m, 2H, H-2', H-6') 6.63 (m, 1H, H-4') 3.75 (s, 6H, 2CH3O)

EXAMPLE 11

2-[4-(3,4-Dimethoxyphenyl)-semicarbazono] indane-1,3-dione 12.50 (s, 1H, NH) 10.19 (s, 1H, NH) 7.97 (s, 4H, H-4, H-5, H-6, H-7) 7.20 (m, 2H, H-2', H-6') 6.92 (d, 1H, H-5', J H5'–6'=8.8 MHz) 3.75 (s, 3H, CH3O) 3.73 (s, 3H, CH3O)

EXAMPLE 12

2-[4-(2-Chloro-5-methoxyphenyl)-semicarbazono] indane-1,3-dione 12.63 (s, 1H, NH) 9.86 (s, 1H, NH) 7.93 (s, 4H, H-4, H-5, H-6, H-7) 7.62 (d, 1H, H-6', J H4'–6'=3.0 Hz) 7.40 (d, 1H, H-3', J H3'–4'=8.8 Hz) 6.76 (dd, 1H, H-4', J H3'–4'=8.8 Hz & J H4'–6'=3.0 Hz) 3.76 (s, 3H, CH3O)

EXAMPLE 13

2-(4,4-Diphenylsemicarbazono)indane-1,3-dione 12.48 (s, 1H, NH) 7.93 (m. 5H, Ph) 7.89 (s, 4H, H-4, H-5, H-6, H-7) 7.85 (m, 5H, Ph)

EXAMPLE 14

2-[4-(2-Methylphenyl)-semicarbazono]indane-1,3-dione 12.57 (s, 1H, NH) 9.63 (s, 1H, NH) 7.97 (s, 4H, H-4, H-5, H-6, H-7) 7.60 (d, 1H, H-6', J H 5'–6'=7.7 Hz) 7.23 (m, 2H, H-3', H-5') 7.14 (m, 1H, H-4') 2.27 (s, 3H, CH3)

EXAMPLE 15

2-[4-(3-Methylphenyl)-semicarbazono]indane-1,3-dione 12.51 (s, 1H, NH) 10.29 (s, 1H, NH) 7.97 (s, 4H, H-4, H-5, H-6, H-7) 7.38 (m, 2H, H-2', H-6') 7.24 (t, 1H, H-5', J H4'–5' & J H5'–6'=7.3 Hz) 6.90 (d, 1H, H-4',J H4'–5'=7.3 Hz) 2.30 (s, 3H, CH3)

EXAMPLE 16

2-[4-(4-Methylphenyl)-semicarbazono]indane-1,3-dione 12.47 (s, 1H, NH) 10.26 (s, 1H, NH) 7.96 (s, 4H, H-4, H-5, H-6, H-7) 7.48(d, 2H, H-2', H-6', J H2'–3' & J H5'–6'= 8.3 Hz) 7.14(d, 2H, H-3', H-5', J H2'–3' & J H5'–6'=8.3 Hz) 2.26 (s, 3H, CH3)

EXAMPLE 17

2-[4-(4-Propylphenyl)-semicarbazono]indane-1,3-dione 12.50 (s, 1H, NH) 10.29 (s, 1H, NH) 7.97 (s, 4H, H-4, H-5, H-6, H-7) 7.48 (d, 2H, H-2', H-6', J H2'–3' & J H5'–6'=8.3 Hz) 7.16 (d, 2H, H-3', H-5', J H2'–3' & J H5'–6'=8.3 Hz) 2.50 (m, 2H, CH2) 1.57 (m, 2H, CH2) 0.89 (t, 3H, CH3, J CH3-CH2=6.8 Hz)

EXAMPLE 18

2-[4-(4-Tert-butylphenyl)-semicarbazono] indane-1,3-dione 12.50 (s, 1H, NH) 10.29 (s, 1H, NH) 7.97 (s, 4H, H-4, H-5, H-6, H-7) 7.49 (d, 2H, H-2', H-6', J H2'–3' & J H5'–6'=8.3 Hz) 7.36 (d, 2H, H-3', H-5', J H2'–3' & J H5'–6'=8.3 Hz) 1.27 (s, 9H, t-Bu)

EXAMPLE 19

2-[4-(2-Chlorophenyl)-semicarbazono] indane-1,3-dione 12.61 (s, 1H, NH) 9.91 (s, 1H, NH) 7.98 à 7.91 (1s, 5H, H-4, H-5, H-6, H-7, H-6') 7.53 (d, 1H, H-3', J H3'–4'=7.3 Hz) 7.38 (t, 1H, H-5', J H5'-4' & J H5'–6'=7.3 Hz) 7.20 (t, 1H, H-4', J H3'–5' & J H4'–5'=7.3 Hz)

EXAMPLE 20

2-[4-(2-Chloro-6-methylphenyl)-semicarbazono]indane-1,3-dione 12.45 (s, 1H, NH) 9.82 (s, 1H, NH) 7.98 (s, 4H, H-4, H-5, H-6, H-7) 7.37–7.24 (m, 3H, H-3', H-4', H-5') 2.49 (s, 3H, CH3)

EXAMPLE 21

2-[4-(4-Chlorophenyl)-semicarbazono] indane-1,3-dione 12.50 (s, 1H, NH) 10.47 (s, 1H, NH) 7.97 (s, 4H, H-4, H-5, H-6, H-7) 7.60 (d, 2H, H-2', H-6', J H2'–3' & J H5'–6'=8.8 Hz) 7.40 (d, 2H, H-3', H-5', J H2'–3' & J H5'–6'=8.8 Hz)

EXAMPLE 22

2-[4-(2,5-Diethoxyphenyl)-semicarbazono] indane-1,3-dione 12.50 (s, 1H, NH) 9.52 (s, 1H, NH) 7.99 (s, 4H, H-4, H-5, H-6, H-7) 7.71 (d, 1H, H-6', J H4'–6'=2.9 Hz) 7.00 (d, 1H, H-3', J H3'–4'=8.8 Hz) 6.63 (dd, 1H, H-4', J H3'–4'=8.8 Hz & J H4'–6'=2.9 Hz) 4.06 (q, 2H, CH2) 3.90 (q, 2H, CH2) 1.38 (m, 6H, 2CH3)

EXAMPLE 23

2-(4-Ethylthiosemicarbazono)-indane-1,3-dione 12.57 (s, 1H, NH) 9.68 (s, 1H, NH) 7.97 (s, 4H, H-4, H-5, H-6, H-7) 3.63 (q, 2H, CH2, J CH3-CH2=6.35) 1.17 (d, 3H, CH3, J CH3-CH2=6.35)

EXAMPLE 24

2-(4-Methylthiosemicarbazono)-indane-1,3-dione 12.62 (s, 1H, NH) 10,00 (s, 1H, NH) 7.98 (s, 4H, H-4, H-5, H-6, H-7) 3.07 (s, 3H, CH3)

EXAMPLE 25

2-[4-(4-Ethylphenyl)-semicarbazono]-indane-1,3-dione 12.50 (s, 1H, NH) 10.27 (s, 1H, NH) 7.97 (s, 4H, H-4, H-5, H-6, H-7) 7.48 (d, 2H, H-2', H-6') 7.17 (d, 2H, H-3', H-5') 3.33 (q, 2H, CH2) 1.17 (m, 3H, CH3)

EXAMPLE 26

2-[4-(3-Ethoxyphenyl)-semicarbazono]-indane-1,3-dione 12.57 (s, 1H, NH) 10.30 (s, 1H, NH) 7.95 (s, 4H, H-4, H-5, H-6, H-7) 7.30 (m, 3H, H-2', H-5', H-6') 7.05 (d, 1H, H-4', J H4'–5'=7.8 Hz) 3.93 (q, 2H, CH2, J CH3-CH2=6.35) 1.35 (t, 3H. CH3, J CH3-CH2=6.35)

EXAMPLE 27

2-[4-(4-Ethoxyphenyl)-semicarbazono]-indane-1,3-dione 12.47 (1s, 1H, NH) 10.17 (1s, 1H, NH) 7.97 (s, 4H, H-4, H-5, H-6, H-7) 7.45 (d, 2H, H-2', H-6', J H2'–3'=8.8 Hz & H5'–6'=8.8 Hz) 6.90 (d, 2H, H-3', H-5', J H2'–3'=8.8 Hz & H5'–6'=8.8 Hz) 3.98 (q, 2H, CH2, J CH3-CH2=6.8) 1.34 (t, 3H, CH3, J CH3-CH2=6.8)

EXAMPLE 28

2-[4-(2,4-Dichlorophenyl)-semicarbazono]-indane-1,3-dione 12.66 (s, 1H, NH) 10,01 (s, 1H, NH) 8.04 (s, 4H, H-4, H-5, H-6, H-7) 7.97 (d, 1H, H-6') 7.85 (s, 1H, H-3') 7.47 (d, 1H, H-5')

EXAMPLE 29

2-[4-(3,4-Methylenedioxyphenl)-semicarbazono]-indane-1,3-dione 12.44 (s, 1H, NH) 10,23 (s, 1H, NH) 7.96 (s, 4H, H-4, H-5, H-6, H-7) 7.23 (s, 1H, H-2') 6.90 (m, 2H, H-5', H-6') 5.99 (s, 2H, CH2)

EXAMPLE 30

2-[4-(2-Fluorophenyl)-semicarbazono]-indane-1,3-dione 12.70 (s, 1H, NH) 10,30 (s, 1H, NH) 8.04 (m, 1H, H-3') 7.97 (s, 4H, H-4, H-5, H-6, H-7) 7.20 (m, 3H, PHe)

EXAMPLE 31

2-[4-(3-Fluorophenyl)-semicarbazono]-indane-1,3-dione 12.50 (s, 1H, NH) 10,56 (s, 1H, NH) 7.98 (s, 4H, H-4, H-5, H-6, H-7) 7.57 (d, 1H, H-6', J H5'–6'=10.25 Hz) 7.41 (m, 2H, H-2', H-4') 7.30 (m, 1H, H-5')

EXAMPLE 32

2-[4-(4-Fluorophenyl)-semicarbazono]-indane-1,3-dione 12.30 (s, 1H, NH) 10,41 (s, 1H, NH) 7.98 (s, 4H, H-4, H-5, H-6, H-7) 7.60 (m, 2H, H-3', H-5') 7.20 (m, 2H, H-2', H-6')

EXAMPLE 33

2-[4-(2-Bromophenyl)-semicarbazono]-indane-1,3-dione 12.47 (s, 1H, NH) 9.70 (s, 1H, NH) 7.98 (s, 4H, H-4, H-5, H-6, H-7) 7.84 (d, 1H, H-3', J H3'–4'=8.3 Hz) 7.68 (d, 1H, H-6', J H5'–6'=8.3 Hz) 7.43 (t, 1H, H-5', J H5'–6' & 4'–6'=8.3 Hz) 7.16 (t, 1H, H-4', J H3'–4' &: H54'-5'=8.3 Hz)

EXAMPLE 34

2-[4-(4-Bromophenyl)-semicarbazono]-indane-1,3-dione 12.44 (s, 1H, NH) 10.36 (s, 1H, NH) 7.96 (s, 4H, H-4, H-5, H-6, H-7) 7.53 (s, 4H, H-2',H-3',H-5', H-6')

EXAMPLE 35

2-[4-(2-Hydroxyethyl)-semicarbazono]-indane-1,3-dione 12.11 (s, 1H, NH) 10.20 (s, 1H, NH) 7.96 (s, 5H, H-4, H-5, H-6, H-7, NH) 4.78 (t, 1H, OH) 3.47 (m, 2H, CH2-N) 3.27 (m, 2H, CH2-O)

EXAMPLE 36

2-[4-(2-Acetoxyphenyl)-semicarbazono]-indane-1,3-dione 12.51 (s, 1H, NH) 9.78 (s, 1H, NH) 7.97 (s, 4H, H-4, H-5, H-6, H-7) 7.80 (m, 1H, H-3') 7.28 (m, 3H, H-4', H-5', H-6') 2.38 (s, 3H, CH3)

EXAMPLE 37

5-methoxy-2-(4-phenylsemicarbazono)-indane-1,3-dione 12.45 (s, 1H, NH) 10.26 (s, 1H, NH) 7.90 (d, 1H, H-7, J H6–7=7.8 Hz) 7.58 (d, 1H. H-6, J H6–7=7.8 Hz) 7.38 (m,–5H, H-2', H-3', H-5', H-6', H4) 7.07 (m, 1H, H-4') 3.99 (s, 3H, OCH3)

EXAMPLE 38

5-Methoxy-2-(4-phenylthiosemicarbazono)-indane-1,3-dione 12.85 (1s, 1H, NH) 11.17 (s, 1H, NH) 7.96 (d, 1H, H-7, J H6–7=7.8 Hz)) 7.59 (d, 1H, H-6, J H6–7=7.8 Hz)) 7.45 (m, 4H, Ph) 7.27 (m, 1H, Ph) 3.99 (s, 3H, OCH3)

EXAMPLE 39

5-methoxy-2-semicarbazono-indane-1,3-dione 11.94 (s, 1H, NH) 7.90 (d, 1H, H-7, J H6–7=8.3 Hz) 7.87 (m, 4H, H-4, H-6, NH2) 3.98 (s, 3H, CH3O)

EXAMPLE 40

5-methoxy-2-[4-(2-Hydroxyphenyl)-semicarbazono]-indane-1,3-dione 12.50 (s, 1H, OH) 10.11 (s, 1H, NH) 9.53 (s, 1H, NH) 7.95 (m, 2H, H-7, H-3') 7.45 (m, 2H, H-4, H-6) 6.85 (m, 3H, H-4', H-5', H-6') 3.99 (s, 3H, CH3O)

EXAMPLE 41

5-methoxy-2-thiosemicarbazono-indane-1,3-dione 12.50 (1s, 1H, NH) 12.41 (s, 1H, SH 9.38 (s, 1H, NH) 7.95 (d, 1H, H-7, J H6–7=7.8 Hz) 7.47 (m, 2H, H-4, H-6) 3.98 (s, 3H, CH3O)

EXAMPLE 42

5-Hydroxy-2-(4-phenylsemicarbazono)-indane-1,3-dione 12.30 (1s, 1H, NH) 11.70 (1s, 1H, NH) 10.29 (1s, 1H, OH) 7.87 (d, 1H, H-6, JH5–6=8.3 Hz) 7.60 (d, 1H, H-5, JH5–6=8.3 Hz) 7.35 (m, 3H, H-4, H-2', H-6') 7.28 (m, 2H, H-3', H-5') 7.18 (m, 1H, H-4')

EXAMPLE 43

5-Hydroxy-2-semicarbazono-indane-1,3-dione 11.90 (1s, 1H, NH) 7.84 (d, 1H, H-7, J H6–7=8.3 Hz) 7.30 (m, 4H, H-4, H-6, NH2)

EXAMPLE 44

5-Hydroxy-2-(4-phenylthiosemicarbazono)-indane-1,3-dione 11.96 (s, 1H, NH) 11.12 (s, 1H, NH) 7.84 à 7.20 (m, 8H, Ph)

EXAMPLE 45

5-Hydroxy-2-thiosemicarbazono-indane-1,3-dione 12.55 (1s, 1H, NH) 12.42 (s, 1H, OH) 9.36 (s, 1H, SH) 8.78 (s, 1H, NH) 7.89 (d, 1H, H-7, J H6–7=8.3 Hz) 7.27 (m, 2H, H-4, H-6)

EXAMPLE 46

5,6-Dimethoxy-2-semicarbazono-indane-1,3-dione 11.78 (s, 1H, NH) 7.39 (s, 1H, H-4) 7.35 (s, 1H, H-7) 7.26.(s, 2H, NH2) 3.98 (s, 6H, 2CH3)

EXAMPLE 47

5,6-Dimethoxy-2-(4-phenylsemicarbazono)-indane-1,3-dione 12.30 (s, 1H, NH) 10.18 (s, 1H, NH) 7.59 (m, 7H, H-4, H-7, Ph) 3.99 (s, 6H, 2CH3)

EXAMPLE 48

2-[4-(3-Trifluoromethylphenyl)-semicarbazono]-indane-1,3-dione 12.50 (1s,1H, NH) 10.68 (s, 1H, NH) 8.05 (s, 1H, H2') 7.99 (s, 4H, H-4, H-5, H-6, H-7) 7.83 (d, 1H, H-4', J H4'–5'=7.8 Hz) 7.60 (t, 1H, H-5', J H4'–5'=& JH5'–6'=7.8 Hz) 7.44 (d, 1H, H-6', J H5'–6'=7.8 Hz)

EXAMPLE 49

2-[4-(2-Trifluoromethylphenyl)-semicarbazono]-indane-1,3-dione 12.57 (1s, 1H, NH) 9.85 (s, 1H, NH) 7.09 (s. 4H, H-4, H-5, H-6, H-7) 7.80 (m, 3H, H-3', H-5', H-6') 7.74 (m, 1H, H-3')

EXAMPLE 50

2-[4-(3-Bromophenyl)-semicarbazono]-indane-1,3-dione 12.44 (s, 1H, NH) 10.48 (s, 1H, NH) 7.93 (s, 4H, H-4, H-5, H-6, H-7) 7.87 (s, 1H, H-2') 7.45 (d, 1H, H-4', JH4'–5'=6.3 Hz) 7.25 (m, 2H, H-5', H-6')

EXAMPLE 51

2-[4-(4-Bromophenyl)-thiosemicarbazono]-indane-1,3-dione 12.88 (s, 1H, NH) 10.48 (s, 1H, NH) 8.02 (s, 4H, H-4, H-5, H-6, H-7) 7.60 (s, 4H, H-2', H-3', H-5', H-6')

EXAMPLE 63

1,2-(4-Phenylsemicarbazono)-3-indanone 11.80 (s, 2H, NH) 9.80 (s, 2H, NH) 7.97 (m, 2H, H-4, H-7) 7.65 (m, 6H, H-5, H-6, 2H-2', 2H-6') 7.56 (m, 4H, 2H-3', 2H-5') 7.16 (m, 2H, 2H-4')

EXAMPLE 64

1-Oximino-2-(4-phenylsemicarbazono)-3-indanone 13.20 (s, 1H, NH) 11.65 (s, 1H, OH) 9.75 (s, 1H, NH) 8.56 (d, 1H, H-7, J H6-H7=7.14 Hz) 7.80 (m, 3H, H-4, H-5, H-6) 7.40 (m, 2H, h-3', H-5') 7.17 (m, 1H, H-4')

EXAMPLE 65

1,3-Dioximino-2-(4-phenylthiosemicarbazono)-3-indanone 13.06 (1s, 1H, NH) 12.59 (1s, 1H, OH) 11.63 (1s, 1H, OH) 9.19 (1s, 1H, NH) 8.56 (d, 1H, H-7, H-4, J H6–7 & J H4–5=7.3 Hz) 7.64 (m, 4H, H-5, H-6, H-2', H-6') 7.33 (t, 2H, H-3', H-5', J H2'–3' & JH5'–6'=7.3 Hz) 7.03 (t, 1H, H-4', J H3'–4' & JH4'–5'=7.3 Hz)

A study of the compounds according to the invention has shown that they have various pharmacological properties. For example they are venotonic and in most cases do not affect the arterial system. They also increase the capillary resistance, reduce vascular hyperpermeability induced by certain inflammatory agents and have antilipoperoxidising, antiradical and anti-inflammatory properties and activity in septic shock.

These properties are shown in mammals such as rats, guinea-pigs and rabbits, under in vitro (isolated vessels or vascular networks) and in vivo conditions.

In the in vitro test, the compounds were solubilised in aqueous solution, either pure or containing DMSO or alcohol.

In the in vivo test, the products were administered intravenously in the form of a pure aqueous solution or intraperitoneally in the form of an aqueous solution optionally containing DMSO or orally in solution or in suspension in carboxymethyl cellulose or in a composite aqueous solution containing Tween® and DMSO in certain cases.

Pharmacological Study Models

The contractile effect was measured in vitro:
  by the contractile force exerted by vascular rings, either quiescent or stimulated (electrically or by physiological agents) and maintained under isometric conditions, and
  by the pressure exerted by vascular networks perfused at a constant flow rate.

In vivo, the arterial and venous pressure was measured under normal conditions and after cardiac arrest. During cardiac arrest, the venous tone was calculated from the venous and arterial pressure measured at equilibrium and corrected in dependence on the relative differences in compliance between these two networks (Samar and Coleman, Am. J. Physiol., 1978, 234:H94–100; Yamamoto et al., Am. J. Physiol., 1980, 238:H823–828).

The increase in capillary resistance was estimated by modification of the petechial index (negative pressure inducing extravasation of erythrocytes) measured by a method derived from the Parrot angiosterrometer.

The vascular permeability was studied in vivo and in vitro by measuring the extravasation of albumin or dye binding the albumin (Evans Blue). In vivo, hyperpermeability was induced by injection of a solution of histamine, bradykinin or zymosan. The in vitro models were used to obtain hyperpressure (over an isolated vascular region) and/or inflammatory vascular reactions.

The anti-inflammatory activity was demonstrated by measuring the inhibition of oedema and leucocyte migration after induction of pleurisy in the rat by injection of carrageenin into the pleural cavity (Almeida et al., J. Pharmacol. Exp. Therap., 1980, 214:74).

The overall "free radical trapping" effect was studied in vitro in a model using 1,1-diphenyl-2-picrylhydrazyl (DPPH) as stable free radical, the method being derived from that described by Lamaison et al., Plantes Médic. et phytothéraphie, XXII, 1988, 231–234.

The anti-oxidising activity was studied in vitro using a lipid peroxidation model based on peroxidation of an emulsion of linoleic acid by iron, the method being a modification of that described by Sutherland et al., Arch. Biochem. Biophys. 1982, 214, 1–11.

The activity in septic shock was studied in the rat after induction by a lipopolysaccharide endotoxin (15 mg/kg), the method being similar to that described by Terashita et al., Eur. J. Pharmacol., 109, 257–261, 1985.

Examples of Pharmacological Effects

The compounds according to the invention increase the contraction of animal saphena veins produced by noradrenalin and depolarisation (hyperpotassic solution) without in most cases affecting the arterial contractile responses. For example, the compounds in Examples 3, 5 and 32 (10 nM to 30 μM) produce a more than 50% increase ($ED_{50} \pm 0.3$ microM) in contractions of the saphena veins of rabbits produced by KCl (40 mM).

The compound in Example 32, at its maximum concentration, increases by 30 to 200% the contraction of the saphena veins in the rabbit in response to 0.3 micromolar noradrenalin.

The compounds in Examples 3 and 32 produce a more than 20% increase in the basic venous tone of the rat without affecting the arterial pressure at doses of 1 to 3 picomols administered intravenously.

By way of illustration, the compound in Example 4 increases the basic capillary resistance by 10 to 100%, when measured one to two hours after administration of 5–20 mg/kg intraperitoneally and up to 4 to 6 hours after oral administration of 5–20 mg/kg to the rat.

The compound in Example 8 reduces vascular permeability by 10 to 50% when measured one to two hours after intraperitoneal administration of 5–20 mg/kg and 2 to 4 hours after oral administration of 5–20 mg/kg to the rat.

The compound in Example 3, administered intraperitoneally twice in doses of 20 mg/kg, inhibits oedema and leucocyte migration in the pleural cavity, six hours after injection of carrageenin in the model of pleurisy in the rat.

The compound in Example 1 has a maximum anti-radical effect of more than 95% in the model using DPPH.

The compound in Example 3, at intravenous doses as low as 1 microgram/kg, produces a more than 30% reduction in the initial drop in arterial pressure produced by the endotoxin and restores the arterial pressure after 30 minutes, where it remains reduced by 30% in the control rats.

Toxicity

The compounds according to the invention have very low toxicity. For example after a single oral administration to the mouse, no deaths were observed at a dose of 1 g/kg of the compounds in Examples 3 and 32. The only observed effects, in certain cases, were coloured diarrhoea and coloured urine, the latter being evidence of resorption of the product.

As the preceding shows, the compounds according to the invention can be used in human and animal therapy. They are particularly indicated, with regard to their vascular and anti-inflammatory components, in functional, organic venous insufficiency and morbid haemorrhoid states and in typically inflammatory complaints (osteo-articular, dermatological or cardio-vascular) and in states of shock consisting of a considerable drop in arterial pressure, more particularly in states of septic (endotoxic) shock.

Functional venous insufficiency is characterised by dilation and hyperdistensibility of the surface veins of the lower limbs accompanied by functional symptoms, i.e. pain in the lower limbs, oedema, and paraesthesia, e.g. tingling and fidgety legs. This morbid state may develop into organic venous insufficiency (varicose veins, deep valvular incontinence, etc) or into phlebo-thrombosis or ulcerous lesions.

In these venous states, an inflammatory component appears in the first stages and is shown more clearly in the advanced stages.

The invention therefore comprises use of the aforementioned compounds as active substances in the preparation of drugs and pharmaceutical compositions for human or veterinary use and comprising at least one of the aforementioned compounds in association with a physiologically acceptable excipient or diluent.

The form of the drugs and pharmaceutical compositions will of course depend on the desired method of administration, inter alia oral, parenteral or rectal, and they can be formulated by conventional methods with usual excipients and vehicles.

For example in the case of oral administration, they can be in the form of pills, tablets, capsules, solutions, syrups or suspensions.

The pills, tablets and capsules contain the active substance together with a diluent (e.g. lactose, dextrose, sucrose, mannitol, sorbitol or cellulose), a lubricant (e.g. silica, talc or stearate, e.g. magnesium stearate), a binder (e.g. starch, methyl cellulose or gum arabic) and a disintegrating agent (e.g. alginate) and are manufactured by known methods such as mixing, granulation, pelleting or coating.

The excipient in syrups can be glycerol, mannitol and/or sorbitol. The solutions and suspensions can contain water and an excipient such as a natural gum or gelose or sodium alginate or polyvinyl alcohol.

For parenteral administration, the drugs or composition can be in the form of solutions, emulsions or suspensions containing the active substance and a suitable excipient such as sterile water or sterile aqueous isotonic saline solutions.

For rectal administration, they can be in the form of suppositories containing the active substance and a suitable excipient such as cocoa butter or polyethylene glycol.

The therapeutic dose of the active substances can be up to 1000 mg per day, depending on the method of administration, the age, weight and state of the patient, and the therapeutic power of the active substance.

We claim:

1. Indan compounds of the formula:

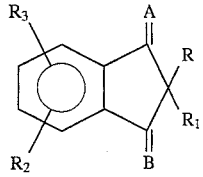

wherein $R_2$ and $R_3$ each independently represent H, $C_1$–$C_4$ alkoxy or OH, and:

a) each of A and B is an oxygen atom and R and $R_1$ together form a group of the formula:
1) =NNHCONHR$_5$ where $R_5$ represents H, pyridyl, phenyl or phenyl substituted by one, two or three groups selected from OH, CF$_3$, $C_1$–$C_4$ alkyl, $C_1$–$C_4$ alkoxy, halogen, or hydroxyethyl;
2) =NNHCON (phenyl)$_2$,; or
3) =NNHCONHNHR$_5$ where $R_5$ is the same as defined above; or b) A is a N—OH group and B is an oxygen atom and R and $R_1$ together form a =NNHCONHR$_5$ group or a =NNHCON (phenyl)$_2$ group, where $R_5$ is the same as defined above; or c) A is a NNHCONHR$_5$ group and B is an oxygen atom and R and $R_1$ together form a =NNHCONHR$_5$ group, where $R_5$ is the same as defined above; or d) each of A and B is a N—OH group and R and $R_1$ together form a =NNHCONHR$_5$ group or a =NNHCON (phenyl)$_2$ group, where $R_5$ is the same as defined above and acid addition salts of salt-forming compounds of formula (I).

2. The indan compounds of claim 1, wherein each of A and B is an oxygen atom.

3. The indan compounds of claim 1, wherein A is a N—OH group and B is an oxygen atom.

4. The indan compounds of claim 1, wherein A is a NNHCONHR$_5$ group and B is an oxygen atom.

5. The indan compounds of claim 1, wherein A and B are each a N—OH group and R and $R_1$ together form a =NNHCONHR$_5$ group.

6. The indan compounds of claim 1, wherein each of A and B is an oxygen atom and R and $R_1$ together form a =NNHCONHR$_5$ group.

7. The indan compounds of claim 1, wherein each of A and B is an oxygen atom and R and $R_1$ together form a =NNHCON(phenyl)$_2$ group.

8. The indan compounds of claim 1, wherein each of A and B is an oxygen atom and R and $R_1$ together form a =NNHCONHNHR$_5$ group.

9. The indan compounds of claim 1, wherein A is a N—OH group and B is an oxygen atom and R and $R_1$ together form a =NNHCONHR$_5$ group.

10. The indan compounds of claim 1, wherein A is a N—OH group and B is an oxygen atom and R and $R_1$ together form a =NNHCON(phenyl)$_2$ group.

11. The indan compounds of claim 1, wherein each of A and B is a N—OH group and R and $R_1$ together form a =NNHCONHR$_5$ group.

12. The indan compounds of claim 1, wherein each of A and B is a N—OH group and R and $R_1$ together form a =NNHCON(phenyl)$_2$ group.

13. 2-(4-phenyl semicarbazono)-indan-1,3-dione.

14. A pharmaceutical composition comprising at least one compound or pharmaceutically acceptable salt thereof of claim 1 and a physiologically acceptable excipient or diluent.

15. A method for the treatment of functional organic venous insufficiency states, morbid hemorrhoid states, inflammatory complaints, states of shock consisting of a considerable drop in arterial pressure and states of septic shock, in human or animal, which comprises administering to a human or animal in need of such a treatment an effective amount of a compound or salt thereof of claim 1.

* * * * *